United States Patent [19]

Rohr et al.

[11] 4,128,469

[45] Dec. 5, 1978

[54] ELECTROCHEMICAL SENSOR

[75] Inventors: Franz-Josef Rohr, Abtsteinach; Rudolf Krapf, Leimen, both of Germany

[73] Assignee: Brown, Boveri & Cie AG, Mannheim-Kafertal, Germany

[21] Appl. No.: 816,174

[22] Filed: Jul. 15, 1977

[30] Foreign Application Priority Data

Jul. 17, 1976 [DE] Fed. Rep. of Germany ..... 26322496

[51] Int. Cl.² .......................................... G01N 27/46
[52] U.S. Cl. ................................................ 204/195 S
[58] Field of Search .............................. 204/15, 195 S

[56] References Cited

U.S. PATENT DOCUMENTS

| | | | |
|---|---|---|---|
| 3,468,780 | 9/1969 | Fischer | 204/195 S |
| 3,597,345 | 8/1971 | Hickam et al. | 204/195 S |
| 3,657,094 | 4/1972 | Hans et al. | 204/195 S |
| 3,835,012 | 9/1974 | Hemak | 204/195 S |
| 3,960,692 | 6/1976 | Weyl et al. | 204/195 S |
| 4,019,974 | 4/1977 | Weyl et al. | 204/195 S |

FOREIGN PATENT DOCUMENTS 2350253 4/1975 Fed. Rep. of Germany.
2360818 6/1975 Fed. Rep. of Germany ....... 204/195 S Primary Examiner—T. Tung
Attorney, Agent, or Firm—Herbert L. Lerner

[57] ABSTRACT

Electrochemical sensor for determining the oxygen content in gases, particularly in exhaust gases from burners or internal-combustion engines, having an ion-conducting solid-electrolyte tube closed at one end and open at the other end for the entry of reference gas to the interior of the tube, a housing surrounding the open end of the tube, electrodes on the inner and outer surfaces of the tube connected to external leads via contact areas, an insulating hollow body on the open end of the tube between the tube and housing, contact areas on a transversal shoulder, conductor strips from the electrodes to the shoulder, a structural unit in the housing standing on the shoulder, radially disposed electric conductors in the structural unit with the lower ends touching the contact areas and the upper ends forming the external connections, and a spring urging the structural unit against the contact areas.

21 Claims, 6 Drawing Figures

U.S. Patent  Dec. 5, 1978  4,128,469
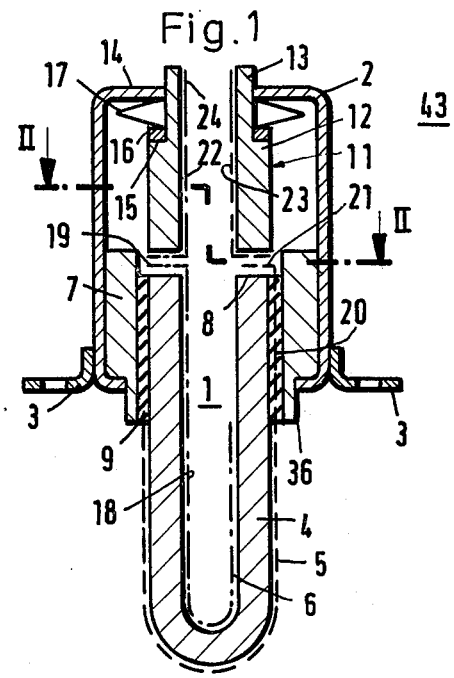
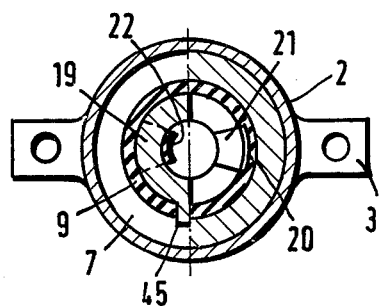
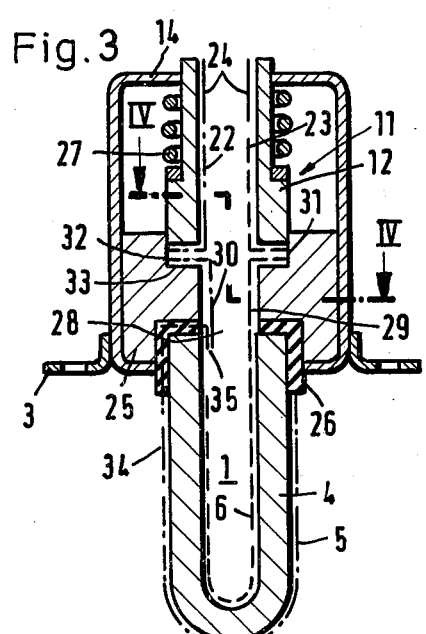
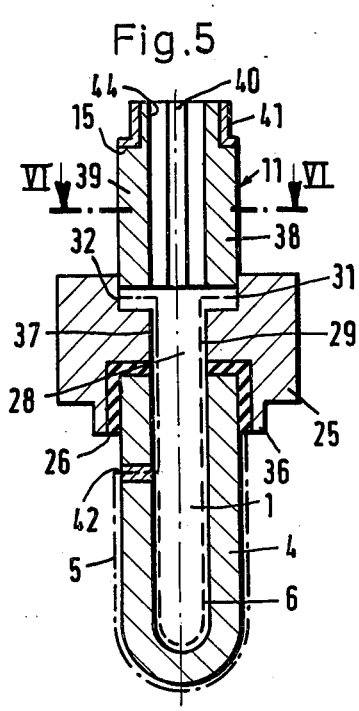
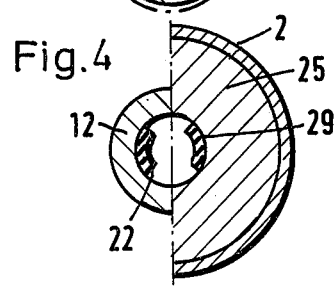
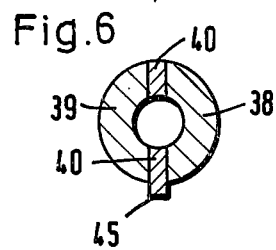

ELECTROCHEMICAL SENSOR

BACKGROUND OF THE INVENTION

1. Field of the Invention

This invention relates to an electrochemical sensor for determining the oxygen content in gases, particularly in exhaust gases of burners or internal-combustion engines, having an ion-conducting solid-electrolyte tube closed on one side, supported by a housing, and electrodes on the inner and outer surfaces of the tube.

2. Description of the Prior Art

In one known sensor of this type, the contact areas are formed in part by the electrodes placed on the inside and outside of the solid-electrolyte tube. The potential leads provided for taking off the voltage each have a resilient, electrically conducting mass which is pressed by means of a spring element into the gap between the outer electrode and the housing as well as into the gap between the inner electrode and a tubular connector part which leads to the outside and is insulated against the housing (German Published Non-Prosecuted Application No. 2 350 253). In addition to the expensive design, particularly because of the potential lead mechanism, the main disadvantage of the known sensor is that the outer electrode is connected to the metallic housing and therefore, to ground. At the ground connection, which is effected via a screw thread at the housing, oxide layers and thus, contact resistances and/or thermoelectric interference voltages readily occur at the high operating temperature of the sensor. Such changes can reduce or falsify the measurement signal. This danger is the greater, as the screw thread is arranged in the immediate vicinity of the sensor tip and therefore, in the proximity of high temperatures.

SUMMARY OF THE INVENTION

It is now an object of the invention to provide an efficient and economical sensor of the type mentioned in which, the electrodes are connected to the outside and insulated against the housing, while the contact points which are under the influence of spring elements as well as the terminals are arranged to be kept as cool as possible.

With the foregoing and other objects in view, there is provided in accordance with the invention an electrochemical sensor for determining the oxygen content in gases, particularly in exhaust gases from burners or internal-combustion engines, having an ion-conducting solid-electrolyte tube supported by a housing with the tube closed on one end and open at the other end for the entry of reference gas to the interior of the tube, an electrode on the inner surface of the tube and an electrode on the outer surface of the tube connected to external leads via contact areas, an insulating hollow body on the open end of the solid-electrolyte tube surrounding the interior or the tube into which carrier gas enters, a housing around the hollow body and extending above the top of the tube and hollow body, contact areas disposed on at least one shoulder facing the top of the housing, conductor strips from the electrodes to the shoulder with the upper ends of the contact strips on the shoulder forming the contact areas, a structural unit in which the leads are combined, disposed in the housing above the tube and standing on the shoulder, the structural unit having radially disposed electric conductors, the lower ends of which extend area-wise over the face of the structural unit and touch the contact areas, and the upper ends of which form the external connections, and a spring element inserted between an outer shoulder of the structural unit and a counter support in the housing.

Other features which are considered as characteristic for the invention are set forth in the appended claims.

Although the invention is illustrated and described herein as embodied in an electrochemical sensor, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which:

FIG. 1 is a central longitudinal cross section of a sensor with an insulating sleeve, in accordance with the invention; and FIG. 2 is a cross section through the sensor along line II—II of FIG. 1; and FIG. 3 is an axial longitudinal cross section through a sensor with an insulating flange; and FIG. 4 is a cross section through the sensor along line IV—IV of FIG. 3, parts situated behind the section plane not being shown; and FIG. 5 is an axial longitudinal section through a variant of the sensor of FIG. 3, the parts of the housing not being shown; and FIG. 6 is a cross section through the sensor along line VI—VI of FIG. 5, parts situated behind the section line not being shown.

DETAILED DESCRIPTION OF THE INVENTION

The contact areas are arranged on at least one transversal shoulder facing the top of the housing. A hollow body surrounds the interior carrying the reference gas and is preferably formed of ceramic material. The hollow body is placed on the open end of the solid-electrolyte tube. The potential leads are combined in a tubular structural unit mounted on the transversal shoulder. The hollow body has electrical conductors which run substantially in the axial direction. The lower ends of the electrical conductors extend area-wise over the end face of the structural unit and touch the contact areas, and the upper ends of the conductors form the external terminals. Spring elements are inserted between an outer shoulder of the structural unit and a countersupport arranged at the housing, preferably the top of the housing. By arranging the contact areas around the interior carrying the reference gas, short connecting paths to the electrodes as well as to the terminals arranged in the vicinity of the housing top are provided. Combining the potential leads in a structural unit insulated against the housing simplifies the design and thereby reduces the costs in spite of the fact that the potential leads are insulated from the housing. The ceramic hollow body not only simplifies the construction and the design of the transversal shoulder; it also at the same time insulates the housing against the hot solid-electrolyte tube. In addition both external terminals are arranged far from the hot sensor tip, thereby, reducing the danger of oxidation.

In one preferred mode, the transversal shoulder is formed by the open end of the solid electrolyte tube. The hollow body consists of a cylindrical insulating sleeve placed over the solid-electrolyte tube, projecting above the open end of the solid-electrolyte tube. The hollow body is fastened by the interposition of a connecting layer, preferably consisting of glass solder. The inner electrode is connected in an electron-conducting manner via a first conductor strip on the inside of the tube to one contact area, and the outer electrode, via a second conductor strip brought through the connecting layer to the other contact area.

The hollow body may be in the form of an insulating, ring-shaped intermediate flange. The upper opening of the flange has a step for forming a transversal shoulder, while in a coaxial lower cut-out the open end of the solid-electrolyte tube is fastened with the interposition of a connecting layer, desirably of glass solder.

In this connection it is advantageous that the one contact area be connected to the inner electrode via a third conductor strip which is arranged on the wall of the central passage opening of the insulating flange. The other contact area which is disposed on the wall of the passage opening, is connected, electrically conducting, to the end of a fifth conductor strip which extends, starting from the outer electrode, through the connecting layer via the end face of the solid-electrolyte tube to about the inner end area of this tube.

Another equally reliable connection is available if one contact area is connected via a third conductor strip arranged on the wall of the central passage opening of the insulating flange to the inner electrode. The other contact area is connected to the outer electrode in an electrically conducting manner via a sixth conductor strip which runs on the wall of the passage opening and the solid-electrolyte tube up to the vicinity of the outer electrode. A connecting element, for instance, in the form of a piece of wire, goes through the wall of the solid-electrolyte tube approximately radially and gas-tight.

The potential leads may be arranged as seventh and eighth conductor strips on the inside of an insulating tube. The conductors extend up to and over the lower end face of the insulating tube and there touch the contact areas. They form, or form in part, terminals for external leads in the upper end region of the insulating tube.

A particularly strong design is obtained if the potential leads consist of semitubular elements, for instance, of metal, which are joined together to form a structural unit by at least one insulating piece. The lower end faces of the conductors touch the contact areas, while the upper end of the structural unit forms a plug socket. The shoulder and the stepped upper end of the structural unit are provided with an insulating layer, for instance, of glass.

In the drawings identical parts are designated in the individual figures with the same reference symbols.

Referring to FIG. 1, the sensor has a cylindrical housing 2 with flanged-over bottom and top, which can be secured at the intended measurement point by means of lugs 3 which are fastened to its lower end. A solid-electrolyte tube 4, for instance, of doped zirconium dioxide, with a closed lower end and a circular cross section protrudes from a lower opening of the housing 2. A catalytically active outer electrode 5 of porous platinum is arranged on the outer surface of this tube. The inside surface of the electrolyte tube 4 has an inner electrode 6. On the upper end of the solid-electrolyte tube 4, a ceramic insulating sleeve 7 which has the shape of a circular cylinder and rests on the housing, is fastened in such a manner that a transversal shoulder 8, which is approximately perpendicular to the longitudinal axis, is formed at the upper end of the solid-electrolyte tube. For fastening the insulating sleeve 7, a connecting layer 9 of glass solder or a material with similar properties is inserted between the former and the solid-electrolyte tube. In order to protect the outer electrode 5 or a conductor strip from contact with the housing 2 at the exit of the solid-electrolyte tube 4 from the housing 2 and to guide the solid-electrolyte tube 4, the insulating sleeve 7 has a lip 36 going through the bottom of the housing 2. The length of the insulating sleeve 7 corresponds preferably approximately to the outside diameter and its diameter to about 1.5 to 2.0-times the outside diameter of the solid-electrolyte tube 4.

The upper, open end of the solid-electrolyte tube 4 is adjoined by the potential-lead unit 11. It consists of an insulating tube 12 which sits on the transversal shoulder 8 of the solid-electrolyte tube 4, has about the same outside diameter as the solid-electrolyte tube 4 and is thereby centered by the protruding upper end of the insulating sleeve 7. As will be seen from FIG. 2 the lower end of the insulating tube 12 has a radially projecting nose 45, which engages in a corresponding recess of the insulating sleeve 7 to prevent any rotary motion of the insulating tube 12 relative to the transversal shoulder 8. The inside diameters of the solid-electrolyte 4 and the insulating tube 12 are approximately equal, so that the interior 1, which carries the reference gas, in the present case, air has an approximately constant cross section. The upper end of the insulating tube 12 is open to the outside atmosphere 43 and has an outer lip 13 which is guided in an opening of the housing top 14 and protrudes somewhat into the outside space 43. On the shoulder 15 formed by the lip 13, an intermediate washer 16 of metal is arranged. As the insulating tube 12 is not fastened on the transversal shoulder 8, but is put in place only loosely, two cup springs 17 are arranged between the housing top 14 and the washer 16, which springs 17 push the insulating tube 12 onto the transversal shoulder 8 of the solid-electrolyte tube 4 and thereby secure it. For the same of clarity, a spacing is shown in the drawings between the transversal shoulder 8 and the structural unit 11.

The inner electrode 6, which does not extend all the way to the upper end of the solid-electrolyte tube, is extended upward via a first conductor strip 18. Here, the upper end 19 of this conductor strip 18 extends over the transversal shoulder 8 of the solid-electrolyte tube 4 and forms a contact area there. The outer electrode 5 is connected, like the inner electrode 6, to a second conductor strip 20, which is brought upward in the connecting layer 9 approximately diametrically opposite to the first conductor strip 18. Electrode 5 extends with its end 21 over the transversal shoulder 8 of the solid-electrolyte tube 4 and forms a second contact area. The contact areas have about the width of the conductor strips and are arranged about diametrically around the opening of the solid-electrolyte tube 4. Platinum is preferably used as material for the conductor strips. Depending on the size of the sensor, the width of the conductor strips is 1 to 10 mm. If very narrow conductor strips are used, one will make the contact areas wider than the conductor strips so that better contact is made. A preferred width of the conductor strips is 2 to 4 mm.

In order to bring the potential of the electrodes 5 and 6 to the outside, a seventh conductor strip 22 and an eighth conductor strip 23 are applied to the inside of the insulating tube 12. These conductor strips lead vertically upward and their dimensions correspond approximately to the conductor strips 18, 20. The seventh and eighth conductor strips 22 and 23 are likewise arranged approximately diametrically opposite to each other, and the lower ends of the conductor strips extend over the lower end face of the insulating tube 12 and touch the contact areas 19 and 21. The upper ends of the seventh and eighth conductor strips 22, 23 end approximately flush with the insulating tube 12. For connecting these conductor strips 22 and 23 to a control or measuring equipment, a plug, not shown, matched to the arrangement of the conductor strips is plugged into the insulating tube 12. Thus, the upper end of the insulating tube 12 serves, so to speak, as a jack. It should be noted here, however, that the interior 1 of the solid-electrolyte tube 4 must not be cut off from its reference gas, i.e. air of the ambient space.

In the variant of the sensor according to FIG. 3, an insulating, ring-shaped intermediate flange 25 is interposed between the upper end of the solid-electrolyte tube 4 and the potential-lead unit 11. The solid-electrolyte tube 4 is fastened in a lower recess, which is coaxial to the passage opening, of the intermediate flange 25 with the interposition of a connecting layer 26, preferably of glass solder or sintered glass ceramic. The insulating tube 12 is centered and supported in an upper coaxial recess of the intermediate flange 25 which recess points toward the housing top 14. The inside diameters of the insulating tube 12, the intermediate flange 25 and the solid-electrolyte tube 4 are approximately equal. The design of the insulating tubes 12 in FIGS. 1 and 3 is the same; the difference is merely that coil springs 27 are provided here for pressing the insulating tube onto the transversal shoulder 33.

Third and fourth conductor strips 29 and 30 are provided approximately diametrically opposite to each other on the walls of the passage opening 28. The upper ends 31, 32 of the third and fourth conductor strips extend in sector-fashion over the transversal shoulder 33 of the upper recess and form the contact areas. The lower end of the conductor strip 29 extends on the inside surface to the inner electrode 6 and is connected there with it. The outer electrode 5 which is brought upward in the region of the connecting layer 26, is connected to a fifth conductor strip 34, and extends in its end region 35 approximately into the interior 1 of the solid-electrolyte tube 4. In this end region 35, the fifth conductor strip 34 is overlapped by the fourth conductor strip 30 and is electrically connected thereto. With respect to the design of the conductor strips, the same considerations apply as were discussed in regard to FIG. 1. If the connecting layer 26 is made of insulating material as in the present embodiment then layer 26 also preferably extends over that region of the outer electrode 5 or the conductor strip 34, respectively, which is located inside the lower housing opening, in order to avoid contact between the housing 2 and the electrode 5 or the conductor strip 34.

As in the variant described above the intermediate flange 25 is made of a material which, in addition to low electric conductivity preferably also exhibits low thermal conductivity, any heat flow from the sensor to the contact areas 31 and 32 is reduced, so that the danger of corrosion and oxidation of these areas is reduced and proper contact is also ensured over extended periods of time. This makes possible the use of non-noble metals for the conductor strips and the contact areas. In order to decrease the heat flow from the sensor to the contact areas effectively, the thickness of the flange 25 in the region between the insulating tube 12 and the solid-electrolyte tube 4 is at least 0.5-times the outside diameter of the solid-electrolyte tube. In order to also reduce the heat conduction to the housing 2, which surrounds the intermediate flange, the ratio of the outside diameter of the solid-electrolyte tube 4 to the outside diameter of the flange is about 1.5 to 1 : 2.

In FIG. 5 the variant of the sensor assembly according to FIG. 3 is shown without the housing. The insulating flange 25 has here at its lower end an outer lip 36, which goes through the lower opening of the housing 2. Exactly as in the embodiment as in FIG. 3, the inner electrode 6 is connected here, too, to a third conductor strip 29, the upper end 31 of which forms a contact area. Approximately diametrically opposite to the conductor strip 29, there is arranged on the wall of the passage opening 28 a sixth conductor strip 37. The upper radial end 32 of conductor strip 37 forms the contact area and the lower portion of conductor strip 37 goes into the solid-electrolyte tube 4. As can be seen in FIG. 5, a connecting element 42 is brought through the wall of the solid-electrolyte tube 4 and is fastened gas-tight by means of glass solder in order to connect the outer electrode 5 to the sixth conductor strip 37 in an electron-conducting manner. It is obvious that the inner surface zone of the solid-electrolyte tube 4, on which the sixth conductor strip 37 is arranged, must be kept free from the inner electrode 6. A piece of corrosionresistant wire, for instance, of platinum, serves preferably as the connecting element 42.

The potential lead unit consists here of two semitubular metal electric conductors 38 and 39 of which are combined by interposed radially disposed insulating pieces 40 to form a tubular structural unit 11. The lower end of the tubular structural unit engages in the upper recess of the intermediate flange 25 and the conductors 38 and 39 of the structural unit touch the contact areas 31 and 32. The tubular design of the potential lead unit can be seen very clearly in FIG. 6, and likewise the projecting nose 45 which is formed by a radial extension of an insulating piece 40. In order to avoid having the potential from conductors 38 and 39 led off via the cup or coil springs which act on the upper shoulder of the potential lead, this step with shoulder 15 is coated with an insulating layer 41, for instance, a glass insulating layer 41. The interior at the upper end of the structural unit 11, here too, forms a jack for receiving a plug and thus, the connections 44 are provided for external leads.

As is evident from the figures, the individual parts of the sensor are substantially revolution-symmetrical with respect to a vertical axis or are arranged diametrically opppsite to each other.

The connecting layers 9 and 26, which consist preferably of glass solder or sintered glass ceramic and thus conduct neither electrons nor ions, in the embodiments of FIGS. 3 to 6, separate the solid-electrolyte tube 4 from the intermediate flange 25. Thereby, the development of additional electrochemical potentials (mixed potentials) in the region of the intermediate flange 25 which, of course, is colder than the solid-electrolyte tube, is largely precluded. This is of importance for the accuracy, as such mixed potentials falsify the electric voltage produced by the sensor.

If the intermediate flange 25 and the insulating tube 12 consist of material which does not conduct ions and electrons, such as magnesium silicate $MG_2(SiO_4)$, magnesium-aluminum spinel $MgO.Al_2O_3$ or sintered glass ceramic of the composition.

$SiO_2$; 35 to 50%
MgO; 50 to 30% and
$Al_2O_3$; 15 to 30%, then the formation of a mixed potential is completely impossible, as the conductor strips running along the intermedite flange 25 and the insulating tube 12 are now electrochemically completely passive. The sensor therefore comprises an electrochemically active zone, which extends over the length of the solid-electrolyte tube, and a passive zone which is formed by the intermediate flange 25 and/or the insulating tube 12. Thereby, a falsification of the measurement results is largely prevented.

There are claimed:

1. In an electrochemical sensor for determining the oxygen content in gases, particularly in exhaust gases from burners or internal-combustion engines, having an ion-conducting solid-electrolyte tube supported by a housing with the tube closed on one end and open at the other end for the entry of reference gas to the interior of the tube, an electrode on the inner surface of the tube and an electrode on the outer surface of the tube connected to external leads via contact areas, the combination therewith of
   (a) an insulating hollow body surrounding the open end of the solid-electrolyte tube,
   (b) a housing around the hollow body and extending above the top of the tube and hollow body,
   (c) contact areas disposed on at least one shoulder facing the top of the housing,
   (d) conductor strips from the electrodes extending to the shoulder with the upper ends of the conductor strips on the shoulder forming the contact areas,
   (e) an insulating structural unit in which the leads are combined, disposed in the housing above the tube and standing on the shoulder,
   (f) said structural unit having electric conductor, the lower ends of which extend area-wise over the face of the structural unit and touch the contact areas, and
   (g) a spring element urging the structural unit against the contact areas.

2. Electrochemical sensor according to claim 1, wherein the insulating hollow body is a ceramic hollow body.

3. Electrochemical sensor according to claim 1, wherein the transversal shoulder is formed by the open end of the solid-electrolyte tube, and the hollow body consists of a cylindrical insulating sleeve which is placed over the solid-electrolyte tube, protrudes above the open end of the solid-electrolyte tube and is fastened to the solid-electrolyte tube with the interposition of a connecting layer, and wherein the inner electrode is connected to one contact area via a first conductor strip disposed on the inside of the tube, and the outer electrode to the other contact area via a second conductor strip brought through the connecting layer.

4. Electrochemical sensor according to claim 3, wherein the connecting layer consists substantially of glass solder.

5. Electrochemical sensor according to claim 3, wherein the connecting layer consists substantially of sintered glass ceramic.

6. Electrochemical sensor according to claim 3, wherein the conductor strips consist of strip-shaped extensions of the electrodes.

7. Electrochemical sensor according to claim 3, wherein the cylindrical insulating sleeve has a lip at the lower end which lip goes through an opening at the bottom of the housing.

8. Electrochemical sensor according to claim 3, wherein the insulating sleeve consists substantially of magnesium silicate $Mg_2(SiO_4)$, magnesium-aluminum spinel $MgO.Al_2O_3$ or sintered glass ceramic of the composition $SiO_2$, 35 to 50%; MgO, 50 to 30%; and $Al_2O_3$, 15 to 20%.

9. Electrochemical sensor according to claim 1, wherein the hollow body is an insulating ring-shaped intermediate flange, the upper opening of which is stepped to form a transversal shoulder, while the open end of the solid-electrolyte tube is fastened in a coaxial lower step with the interposition of a connecting layer.

10. Electrochemical sensor according to claim 9, wherein the connecting layer is glass solder.

11. Electrochemical sensor according to claim 9, wherein the connecting layer is sintered glass ceramic.

12. Electrochemical sensor according to claim 9, wherein the conductor strip leading from the outer electrode comprises two section, one of said sections extending from the outer electrode through the connecting layer over the end face of the solid-electrolyte tube to the other section, which extends along the wall of a central passage opening of the intermediate flange to the shoulder to form one of said contact areas.

13. Electrochemical sensor according to claim 9, wherein the conductor strip for the outer electrode extends through a connecting element which goes through the wall of the solid-electrolyte tube radially and gas-tightly.

14. Electrochemical sensor according to claim 9, wherein the insulating ring-shaped intermediate flange has a lip at the lower end which lip goes through an opening at the bottom of the housing.

15. Electrochemical sensor according to claim 9, wherein the intermediate flange consists substantially of magnesium silicate $Mg_2(SiO_4)$, magnesium-aluminum spinel $MgO.Al_2O_3$ or sintered glass ceramic of the composition $SiO_2$, 35 to 50%; MgO, 50 to 30%; and $Al_2O_3$, 15 to 20%.

16. Electrochemical sensor according to claim 1, wherein the contact areas have approximately the shape of sectors and are disposed approximately diametrically opposite to each other.

17. Electrochemical sensor according to claim 1, wherein said structural unit is in the form of an insulating tube, and two conductor strips extend over the lower end of the insulating tube and there touch the contact areas, and the opposite extension of said conductor strips form potential leads in the upper end region of the insulating tube as connections for external leads.

18. Electrochemical sensor according to claim 17, wherein the insulating tube consists substantially of magnesium silicate $Mg_2(SiO_4)$, magnesium-aluminum spinel $MgO.Al_2O_3$ or sintered glass ceramic of the composition $SiO_2$, 35 to 50%; MgO, 50 to 30%; and $Al_2O_3$, 15 to 20%.

19. Electrochemical sensor according to claim 1, wherein the structural unit consists substantially of magnesium silicate $Mg_2(SiO_4)$, magnesium-aluminum spinel $MgO.Al_2O_3$ or sintered glass ceramic of the composition $SiO_2$, 35 to 50%; MgO, 50 to 30%; and $Al_2O_3$, 15 to 20%.

20. Electrochemical sensor according to claim 1, wherein the spring element is inserted between a shoulder of the structural unit and a counter support in the housing.

21. In an electrochemical sensor for determining the oxygen content in gases, particularly in exhaust gases from burners of internal-combustion engines, having an ion-conducting solid-electrolyte tube supported by a housing with the tube closed on one end and open at the other end for the entry of reference gas to the interior of the tube, an electrode on the inner surface of the tube and an electrode on the outer surface of the tube connected to external leads via contact areas, the combination therewith of
(a) an insulating hollow body surrounding the open end of the solid-electrolyte tube,
(b) a housing around the hollow body and extending above the top of the tube and hollow body,
(c) contact areas disposed on at least one shoulder facing the top of the housing,
(d) conductor strips from the electrodes extending to the shoulder with the upper ends of the conductor strips on the shoulder forming the contact areas, and
(e) a structural unit disposed in the housing above the tube and standing on the shoulder, wherein the structural unit is composed of semitubular conductors of metal as the potential leads, with the semitubular conductors connected together by at least one insulating piece and with the lower end faces of the semitubular conductors touching the contact areas, while the upper end of the structural unit forms a jack as a connection for external leads.

* * * * *